United States Patent
Saito et al.

(10) Patent No.: US 8,524,363 B2
(45) Date of Patent: Sep. 3, 2013

(54) ORGANOSILICONE FINE PARTICLES OF TETRAHEDRAL GENERAL SHAPES, METHOD OF PRODUCTION THEREOF AND COSMETIC MATERIALS, RESIN COMPOSITIONS AND PAINT COMPOSITIONS CONTAINING SAME

(75) Inventors: Chiaki Saito, Gamagori (JP); Motoki Maeda, Gamagori (JP); Eriko Hatta, Gamagori (JP)

(73) Assignee: Takemoto Yushi Kabushiki Kaisha, Gamagori, Aichi (JP)

( * ) Notice: Subject to any disclaimer, the term of this patent is extended or adjusted under 35 U.S.C. 154(b) by 147 days.

(21) Appl. No.: 13/115,456

(22) Filed: May 25, 2011

(65) Prior Publication Data

US 2011/0224308 A1 Sep. 15, 2011

Related U.S. Application Data

(63) Continuation of application No. PCT/JP2010/053965, filed on Mar. 10, 2010.

(51) Int. Cl.
  *B32B 5/16* (2006.01)
  *C07F 7/02* (2006.01)
  *C07F 7/08* (2006.01)

(52) U.S. Cl.
  USPC ........... 428/402; 556/400; 556/465; 556/466; 556/478; 556/487

(58) Field of Classification Search
  CPC .......... B32B 5/16; B32B 27/00; B32B 27/06; C07F 7/02; C07F 7/08
  USPC ................ 428/402, 446, 447; 556/466, 465, 556/478, 487
  See application file for complete search history.

(56) References Cited

U.S. PATENT DOCUMENTS

| | | | |
|---|---|---|---|
| 7,393,911 B2 * | 7/2008 | Noda | 528/10 |
| 8,263,222 B2 * | 9/2012 | Ishikawa et al. | 428/402 |
| 2006/0089478 A1 * | 4/2006 | Noda | 528/10 |
| 2011/0129672 A1 * | 6/2011 | Aratani et al. | 428/402 |
| 2011/0171157 A1 * | 7/2011 | Aratani et al. | 424/78.03 |

FOREIGN PATENT DOCUMENTS

| | | | |
|---|---|---|---|
| JP | 2000-191789 A | * | 7/2000 |
| JP | 2003-128788 A | * | 5/2003 |
| JP | 2003-171465 A | * | 6/2003 |

* cited by examiner

*Primary Examiner* — Hoa (Holly) Le
(74) *Attorney, Agent, or Firm* — Weaver Austin Villeneuve & Sampson LLP

(57) ABSTRACT

Organosilicone fine particles which are capable of responding to the highly advanced requirements of recent years imposed on them for purposes of actual use, including further improvement in optical characteristics such as total light transmittance and haze as well as heat-resistant colorability related to resin compositions, further improvement in usability (extensions and expansions at the time of use) and feeling (stickiness, roughness and durability) related to cosmetic materials and further improvement in matte effect and factual sense related to paint compositions, as well as methods of their production and cosmetic materials, resin compositions and paint compositions containing such particles are provided. Organosilicone fine particles have tetrahedral general shapes with surfaces each having a concave part with an approximately circular opening. The maximum external diameters L of the organosilicone fine particles have an average value in the range of 0.5-20 μm, the average value being taken from arbitrarily selected 20 of a scanning electron microscope photograph image of the organosilicone fine particles.

5 Claims, 1 Drawing Sheet

ORGANOSILICONE FINE PARTICLES OF TETRAHEDRAL GENERAL SHAPES, METHOD OF PRODUCTION THEREOF AND COSMETIC MATERIALS, RESIN COMPOSITIONS AND PAINT COMPOSITIONS CONTAINING SAME

This application is a continuation of International Application No. PCT/JP2010/053965, filed Mar. 10, 2010.

BACKGROUND OF THE INVENTION

This invention relates to organosilicone fine particles, as well as methods of their production and cosmetic materials, resin compositions and paint composition which contain such particles. Fine particles of various substances have been in use in many applications. Their shapes are mostly indefinite, and they are useful and have been playing their respectable roles as industrial materials. In recent years, however, as the characteristics required of them in various applications become highly advanced, there are beginning to appear many situations where fine particles with controlled shapes are desired. As examples, improvements in the optical characteristics in the field of display devices and optical diffusers, miniaturization in size in the field of electronic components, improvements in usability and feeling of cosmetic products and improvements in matte effect and factual sense in the field of paints may be considered. This invention relates to organosilicone fine particles in tetrahedral general shapes, having surfaces each comprising a concave part with an approximately circular opening.

There have been proposed many kinds of fine particles with controlled shapes such as those made of inorganic and organic materials. As for organic fine particles, Japanese Patent Publications Tokkai 09-103804 and 11-292907, for example, considered polystyrene fine particles, Japanese Patent Publication Tokkai 11-116649, for example, considered polyurethane fine particles, Japanese Patent Publication Tokkai 11-140181, for example, considered polyimide fine particles, and Japanese Patent Publication Tokkai 61-159427, for example, considered organosilicone fine particles. While almost all of these prior art fine particles are spherical or nearly spherical, however, there have in recent years been an increasing number of situations wherein problems were encountered by these spherical or nearly spherical fine particles not being able to respond to the highly advanced requirements which are imposed upon them recently for purposes of use as explained above. For organic fine particles with changed shapes, therefore, Japanese Patent Publication Tokkai 07-157672, for example, proposed hollow fine particles having protrusions and indentations, Japanese Patent Publication Tokkai 2000-191788, for example, proposed nearly spherical fine particles having a large number of small indentations on the surface, Japanese Patent Publication Tokkai 2003-171465, for example, proposed fine particles shaped like a rugby ball, and Japanese Patent Publication Tokkai 2003-128788, for example, proposed semispherical fine particles. Such prior art fine particles with changed changes, too, have problems of not being able to fully respond to the highly advanced requirements of recent years imposed on them for purposes of use.

SUMMARY OF THE INVENTION

It is therefore an object of this invention to provide organosilicone fine particles which are capable of responding to the highly advanced requirements of recent years imposed on them for purposes of actual use, including further improvement in optical characteristics such as total light transmittance and haze as well as heat-resistant colorability related to resin compositions, further improvement in usability (extensions and expansions at the time of use) and feeling (stickiness, roughness and durability) related to cosmetic materials and further improvement in matte effect and factual sense related to paint compositions, as well as methods of their production and cosmetic materials, resin compositions and paint compositions containing such particles.

The inventors herein have carried out investigations in order to solve the aforementioned problems and discovered as a result thereof that what are suitable are a special kind of organosilicone fine particles which are generally in tetrahedral shapes, having surfaces each comprising a concave part 11 with an approximately circular opening.

Thus, this invention relates to organosilicone fine particles characterized as being generally in tetrahedral shapes as a whole, each of the surfaces comprising a concave part 11 with an approximately circular opening, and the average of the maximum external diameters (L) of the individual fine particles (taken from 20 arbitrarily selected particles from a scanning electron microscope photograph) being in the range of 0.5-20 μm. The invention also relates to the methods of producing such fine particles, as well cosmetic materials, resin compositions and paint compositions containing such fine particles.

DETAILED DESCRIPTION OF THE INVENTION

Figure 1:
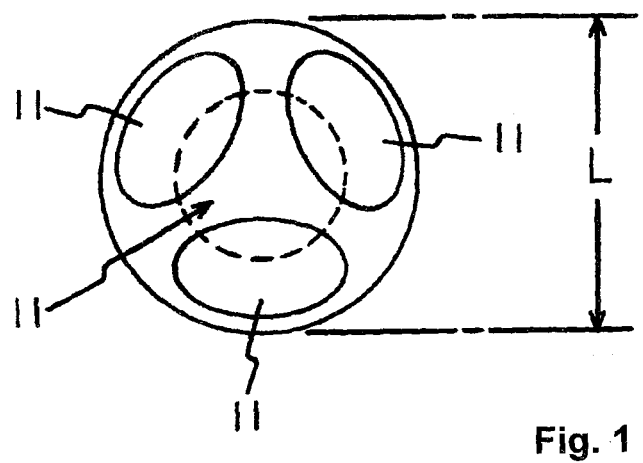
FIG. 1 is an enlarged plan view for approximately showing an organosilicone fine particle embodying this invention.
Figure 2:
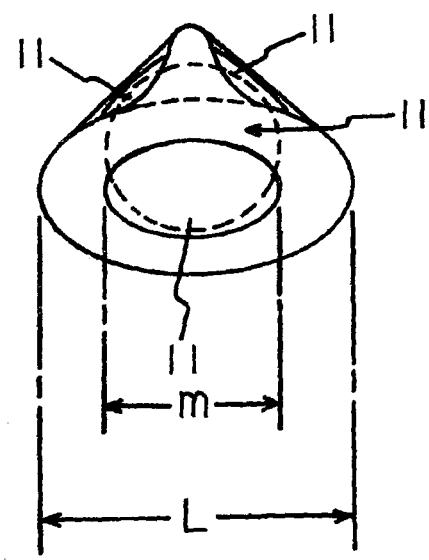
FIG. 2 is a diagonal view for approximately showing the organosilicone fine particle of FIG. 1.
Figure 3:
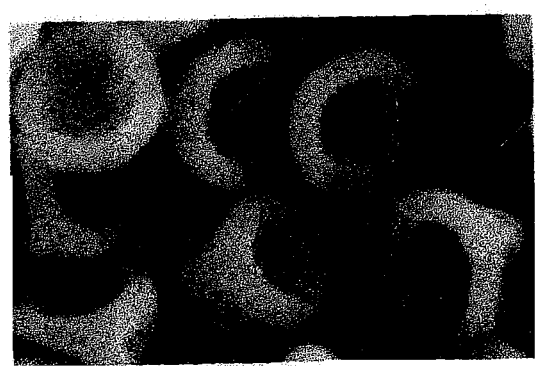
FIG. 3 is a scanning electron microscopic photograph with magnification 3500 for showing an example of organosilicone fine particles embodying this invention.

Organosilicone fine particles according to this invention are explained first. Organosilicone fine particles according to this invention are each a particle having a tetrahedral shape as a whole with each surface comprising a concave part 11 with an approximately circular opening, the average of the maximum external diameters (L) of the individual fine particles being in the range of 0.5-20 μm. In the above, the average value is that taken from 20 arbitrarily selected particles from a scanning electron microscope photograph.

Organosilicone fine particles according to this invention are each tetrahedral in shape as a whole except for the concave parts 11 formed on its surfaces. Of the four surfaces of each particle, the bottom surface is approximately circular, while each of the remaining three surfaces is approximately triangular with the ridgeline and apex parts being rounded. A concave part 11 having an approximately circular opening is formed on each of the four surfaces of the tetrahedral shape such that each concave part 11 has an approximately semi-spherical surface.

Regarding organosilicone fine particles according to this invention, there is no particular limitation on the size of the concave parts 11 formed on their tetrahedral surfaces but it is preferable that the average value of the ratio (m/L) between the maximum diameter (m) and the maximum external diameter (L) of the individual fine particles be in the range of 0.3-0.8. In the above, the average value is to be understood as the value obtained from arbitrarily selected 20 images of particles in a scanning electron microscope photograph.

Organosilicone fine particles of this invention have many characteristics. One of their useful characteristics is the magnitude of oil absorption. Although there is no particular limitation on the magnitude of their oil absorption, it is preferable that this magnitude be in the range of 50-150 ml/100 g.

Organosilicone fine particles of this invention are characterized as comprising siloxane units forming a polysiloxane cross-link structure which forms a three-dimensional network structure. Although the invention does not impose any particular limitation on the kind or ratio of the siloxane units comprising the polysiloxane cross-link structure, those comprising siloxane units shown by $SiO_2$, siloxane units shown by $R^1SiO_{1.5}$, and siloxane units shown by $R^2R^3SiO$, where $R^1$, $R^2$ and $R^3$ are each alkyl group with 1-4 carbon atoms or phenyl group, are preferred.

Examples of $R^1$, $R^2$ and $R^3$ include alkyl groups with 1-4 carbon atoms and phenyl groups such as methyl group, ethyl group, propyl group and butyl group, but methyl group is preferable. Thus, although examples of siloxane units $R^1SiO_{1.5}$ and $R^2R^3SiO$ include methyl siloxane unit, ethyl siloxane unit, propyl siloxane unit, butyl siloxane unit and phenyl siloxane unit, methyl siloxane unit is preferable among these examples.

When the polysiloxane cross-link structure is formed with such siloxane units for organosilicone fine particles of this invention, it is preferable to have siloxane units $SiO_2$ in an amount of 30-50 molar %, siloxane units $R^1SiO_{1.5}$ in an mount of 45-65 molar % and siloxane units $R^2R^3SiO$ in an amount of 3-9 molar % such that the total would be 100 molar %.

Next, a method of producing organosilicone fine particles according to this invention will be described. Organosilicone fine particles according to this invention as described above can be obtained by using silanol group forming silicide $SiX_4$ in an amount of 30-50 molar %, silanol group forming silicide $R^4SiY_3$ in an amount of 45-65 molar % and silanol group forming silicide $R^5R^6SiZ_2$ in an amount of 3-9 molar % such that the total would be 100 molar %, where $R^4$, $R^5$ and $R^6$ are each alkyl group with 1-4 carbon atoms or phenyl group, and X, Y and Z are each alkoxy group with 1-4 carbon atoms, alkoxyethoxy group having alkoxy group with 1-4 carbon atoms, acyloxy group with 2-4 carbon atoms, N,N-dialkylamino group having alkyl group with 1-4 carbon atoms, hydroxyl group, halogen atom or hydrogen atom, obtained by firstly generating silanol compounds by causing silanol group forming silicide $SiX_4$ and silanol group forming silicide $R^5R^6SiZ_2$ to contact water in the presence of a basic catalyst for hydrolysis and then causing a condensation reaction of these silanol compounds with silanol group forming silicide $R^4SiY_3$ in an aqueous condition in the presence of a basic catalyst and an anionic surfactant.

Examples of $R^4$, $R^5$ and $R^6$ include alkyl groups with 1-4 carbon atoms and phenyl groups, among which methyl group is preferable.

Silanol group forming silicide $SiX_4$ is a compound which eventually forms siloxane unit $SiO_2$. Examples of X in $SiX_4$ include (1) alkoxy groups with 1-4 carbon atoms such as methoxy group and ethoxy group, (2) alkoxyethoxy groups having alkoxy group with 1-4 carbon atoms such as methoxyethoxy group and butoxyethoxy group, (3) acyloxy groups with 2-4 carbon atoms such as acetoxy group and propyoxy group, (4) N,N-dialkylamino groups having alkyl group with 1-4 carbon atoms such as dimethylamino group and diethylamino group, (5) hydroxyl group, (6) halogen atoms such as chlorine atom and bromine atom, and (7) hydrogen atom.

Specific examples of silanol group forming silicide $SiX_4$ include tetramethoxy silane, tetraethoxy silane, tetrabutoxy silane, trimethoxyethoxy silane, tributoxyethoxy silane, tetraacetoxy silane, tetrapropyoxy silane, tetra(dimethylamino) silane, tetra(diethylamino)silane, tetrahydroxy silane, chlorosilane triol, dichlorodisilanol, tetrachlorosilane, and chlorotrihydrogen silane, among which tetramethoxy silane, tetraethoxy silane and tetrabutoxy silane are preferred.

Silanol group forming silicide $R^4SiY_3$ is a compound which eventually forms siloxane units $R^1SiO_{1.5}$. Y in $R^4SiY_3$ is similar to X in $SiX_4$ and $R^4$ in $R^4SiY_3$ is similar to $R^1$ in $R^1SiO_{1.5}$.

Specific examples of silanol group forming silicide $R^4SiY_3$ include methyltrimethoxy silane, ethyltriethoxy silane, propyltributoxy silane, butyltributoxy silane, phenyltris(2-methoxyethoxy)silane, methyltris(2-butoxyethoxy)silane, methyltriacetoxysilane, methyltripropyoxy silane, methylsilanetriol, methylchlorodisilanol, methyltrichlorosilane, and methyltrihydrogen silane. As explained above regarding $R^1$ in siloxane units $R^1SiO_{1.5}$, however, those silanol group forming silicides which eventually form methyl siloxane unit, ethyl siloxane unit, propyl siloxane unit, butyl siloxane unit, or phenyl siloxane unit are preferred, and those silanol group forming silicides which come to form methyl siloxane group are more preferred.

Silanol group forming silicide $R^5R^6SiZ_2$ is a compound which eventually forms siloxane units $R^2R^3SiO$. Z in $R^5R^6SiZ_2$ is similar to X in $SiX_4$, and $R^5$ and $R^6$ in $R^5R^6SiZ_2$ are similar to $R^2$ and $R^3$ in $R^2R^3SiO$.

Specific examples of silanol group forming silicide $R^5R^6SiZ_2$ include dimethyldimethoxy silane, diethyldiethoxy silane, dipropyldibutoxy silane, dibutyldimethoxy silane, methylphenyl methoxyethoxy silane, dimethylbutoxyethoxy silane, dimethyldiacetoxy silane, dimethyldipropyoxy silane, dimethyldi(dimethylamino)silane, dimethyldi(diethylamino)silane, dimethyl silane diol, dimethylchlorosilanol, dimethyldicholosilane, and dimethyldihydrogen silane. As explained above regarding $R^2$ and $R^3$ in siloxane units $R^2R^3SiO$, however, those silanol group forming silicides which eventually form dimethyl siloxane unit, diethyl siloxane unit, dipropyl siloxane unit, dibutyl siloxane unit or methylphenyl siloxane unit are preferred, and those eventually form dimethyl siloxane unit are even more preferred.

For producing organosilicone fine particles, silanol group forming silicide $SiX_4$ in an amount of 30-50 molar %, silanol group forming silicide $R^4SiY_3$ in an amount of 45-65 molar % and silanol group forming silicide $R^5R^6SiZ_2$ in an amount of 3-9 molar % are used such that their total would be 100 molar %. Silanol group forming silicide $SiX_4$ and silanol group forming silicide $R^5R^6SiZ_2$ are firstly caused to undergo hydrolysis by contacting water in the presence of a basic catalyst so as to produce a silanol compound. A known kind of basic catalyst may be employed for the hydrolysis. Examples of such a known basic catalyst include inorganic bases such as sodium hydroxide, potassium hydroxide, sodium carbonate, sodium bicarbonate and ammonia and organic bases such as trimethylamine, triethylamine, tetraethyl ammonium hydroxide, dodecyl dimethyl hydroxylethyl ammonium hydroxide and sodium methoxide. It is generally preferable that the basic catalyst to be used for the hydrolysis be at a concentration of 0.001-0.500 mass % with respect to the total silanol group forming silicides used in the reaction.

Next, the silanol compound generated as explained above and silanol group forming silicide $R^4SiY_3$ are caused to undergo a condensation reaction in an aqueous condition in the presence of a basic catalyst and an anionic surfactant. As the basic catalyst for the condensation reaction, as in the case of that for the hydrolysis, those of a known kind can be use, and it is preferable to cause it to be present at a concentration of 0.001-0.500 mass % with respect to the total amount of the silanol group forming silicides used for the reaction.

As the anionic surfactant to be added to the reacting system together with the basic catalyst, too, those of a known kind may be used. Examples of such anionic surfactant include organic sulfates with 8-18 carbon atoms such as octyl sulfate, cetyl sulfate and lauryl sulfate and organic sulfonates with 8-30 carbon atoms such as octyl sulfonate, cetyl sulfonate, lauryl sulfonate, stearyl sulfonate, oleyl sulfonate, p-toluene sulfonate, dodecyl benzene sulfonate, oleyl benzene sulfonate, naphthyl sulfonate and diisoprolyl naphthyl sulfonate. It is preferable to use the anionic surfactant in an amount of 0.001-0.550 mass % with respect to the total amount of the silanol group forming silicides used for the reaction.

The mass ratio of water to the total amount of the silanol group forming silicides is normally 10/90-70/30. The amount of the catalyst to be used varies according to its kind as well as to the kind of the silanol group forming silicide but it is normally 1 mass % or less and preferably in the range of 0.001-0.550 mass % with respect to the total amount of the silanol group forming silicides. The reaction temperature is usually 0-40° C. but preferably 30° C. or less in order to avoid any instantly occurring condensation reaction of the silanol which has been generated by the hydrolysis.

According to this invention, organosilicone fine particles are generated by means of such hydrolysis and condensation reaction of silanol group forming silicides as described above. By the production method according to the present invention, since the catalyst for the hydrolysis can be used also as the catalyst for the condensation reaction, the reaction liquid containing silanol compounds generated by the hydrolysis can be used for the condensation reaction either directly, by further adding a catalyst, or after deactivating or removing the catalyst remaining in the reaction liquid and the silanol group forming silicides which have not reacted. The amount of water used is controlled such that the solid concentration of the organosilicone fine particles in the aqueous suspension will be 2-20 mass %, or preferably 5-15 mass %.

Organosilicone fine particles of this invention can be used as an aqueous material with the solid component adjusted to be 30-70 mass % by separating from the aforementioned aqueous suspension after the hydrolysis and the condensation reaction, say, by passing through a metallic net and through centrifugation or pressure filtration, or they may be used in a dried form. The dried form can be obtained by passing the aqueous suspension through a metallic net, dehydrating by centrifugation or pressure filtration and drying the dehydrated product by heating at 100-250° C. It can also be obtained by a method of heating and drying the aqueous suspension in a vacuum condition or a method of directly heating and drying the aqueous suspension by a spray drier at 100-250° C. It is preferable, however, that such dried materials be crushed, for example, by using a jet mill.

Organosilicone fine particles of this invention thus obtained are tetrahedral as a whole in shape, each of the surfaces comprising a concave part 11 with an approximately circular opening, the average of the maximum external diameters (L) of the individual fine particles being in the range of 0.5-20 μm.

Next, cosmetic materials according to this invention are explained. Cosmetic materials according to this invention are characterized as containing those organosilicone fine particles of this invention described above in an amount of 0.1-10 mass %. Cosmetic materials according to this invention make use of the superior optical characteristics and high oil absorption of the organosilicone fine particles of this invention. When they are used as a basic cosmetic article in a liquid, cream or press form or as an ingredient of a make-up cosmetic article, they are superior in terms of their soft focus effect with reduced roughness and glare, improved coverage of spots on the skin and spread on and fitness to the skin and hence are useful against falling make-up due to sebum.

When a cosmetic material of this invention is produced, other materials such as body pigments, white pigments, pearl pigments, color pigments (dyes), binding ointments, water, surfactants, thickeners, preservatives, antioxidants, and perfumes may be used together with organosilicone fine particles of this invention. Cosmetic materials of this invention can be prepared by any known method for uniformly dispersing such other materials together with organosilicone fine particles of this invention.

Next, resin compositions according to this invention are explained. Resin compositions according to this invention are characterized as containing organosilicone fine particles of this invention described above in an amount of 0.1-10 mass % and are useful where there is a high requirement for improving material characteristics of resin compositions having polymers as main components. In the case of molded resin products requiring advanced optical characteristics such as illumination and display devices, for example, products with high optical transmissivity and haze and improved heat-resistant colorability are becoming desired due to the requirement for highly effective use of light and advanced required functions. Resin compositions of this invention are useful in these fields of application.

Lastly, paint compositions according to this invention are explained. Paint compositions according to this invention are characterized as containing organosilicone fine particles of this invention described above in an amount of 0.1-15 mass % and are useful for providing mold releasability, slippage, antiblocking effect, wear resistance and matte effect to films which have been coated with a paint. In recent years, advanced levels of optical characteristics and improvements in factual sense are required of films and conventional fine particles are no longer able to satisfy the required high levels of matte effect and comfortable factual sense. Paint compositions according to this invention are useful for being able to satisfy such requirements.

The present invention, as explained above, has the merit of providing novel organosilicone fine particles capable of satisfying requirements such as further improvement in optical characteristics such as total light transmittance and haze for resin compositions, further improvement in usability and feeling for cosmetic materials, further improvement in matte effect and factual sense for paint compositions.

In that follows, the invention will be described in terms of test examples but they are not intended to limit the scope of the invention. In the following test examples and comparison examples, "part" will mean "mass part" and "%" will mean "mass %".

Part 1: Synthesis of Organosilicone Fine Particles

TEST EXAMPLE 1

Synthesis of Organosilicone Fine Particles (P-1)

Ion exchange water 2000 g was taken into a reactor vessel and 30% aqueous solution of sodium hydroxide 0.19 g was added thereinto and dissolved. Tetraethoxy silane 308.57 g (1.49 mols) and dimethyldimethoxy silane 22.2 g (0.19 mols) were further added to carry out hydrolysis with stirring at 15°

C. for 60 minutes. An aqueous solution was separately prepared in another reactor vessel by dissolving 10% aqueous solution of dedecylbenzene sodium sulfonate 7.54 g and 30% aqueous solution of hydrochloric acid 2.90 g in ion exchange water 350 g and cooled to 10° C., and the aforementioned hydrolysate solution adjusted to the same temperature was gradually dropped into it with stirring. Methyltrimethoxy silane 277.4 g (2.04 mols) was further added and the whole was left quietly for one hour such that temperature will not exceed 30° C. After it was maintained at the same temperature for 4 hours to carry out condensation reaction, it was caused to undergo condensation reaction thereafter for 10 hours to obtain a white suspension. After the suspension thus obtained was maintained quietly overnight, the white solid phase obtained by removing the liquid phase by decantation was washed with water by a usual method and dried to obtain organosilicone fine particles (P-1).

Regarding organosilicone fine particles (P-1), observations and measurements by a scanning electron microscope photograph image as explained below, measurements of oil absorption, elemental analysis, inductively coupled plasma spectrometry, FT-IR spectrometry and NMR spectrometry were carried out. As a result, it was ascertained that organosilicone fine particles (P-1) were organosilicone fine particles having an overall tetrahedral shape, each surface of which comprising a concave part 11 with an approximately circular opening, the average of the maximum external diameters (L) of the individual particles being 4.9 μm and the average of the ratio (m/L) between the maximum diameter (m) of the concave part 11 and the maximum external diameter (L) of individual particles being 0.65. The organosilicone fine particles thereby obtained had siloxane units $SiO_2$ in the amount of 40 molar %, siloxane units $R^1SiO_{1.5}$ in the amount of 55 molar % and siloxane units $R^2R^3SiO$ in the amount of 5 molar % such that they were together 100 molar %.

Observations and Measurements by Scanning Electron Microscope Photograph

A scanning electron microscope (SEMEDX Type N, produced by Hitachi, Ltd.) was used at magnifications of 2000-5000 to observe organosilicone fine particles (P-1) and obtain a photographic image. From this photographic image, 20 organosilicone fine particles (P-1) were selected arbitrarily and their individual maximum external diameters (L) and the maximum diameters (m) of their concave parts 11 to obtain the average value of L and the average value of m/L.

Measurement of Oil Absorption Value of Organosilicone Fine Particles (P-1)

Measurements were made according to JIS-K5101-13-1 (2004).

Analysis of Constituent Siloxane Units of Organosilicone Fine Particles (P-1)

Organosilicone fine particles (P-1) 5 g were accurately measured and added to 0.05N aqueous solution of sodium hydroxide 250 ml to extract all of the hydrolyzable groups in the organosilicone fine particles. Organosilicone fine particles were separated by ultra-centrifugation from the extraction-processed liquid, and after the separated organosilicone fine particles were washed with water and dried at 200° C. for 5 hours, elemental analysis, inductively coupled plasma spectrometry and FT-IR spectrometry were carried out on them to measure total carbon content and the amount of contained silicon, and silicon-carbon bonding and silicon-oxygen-silicon bonding were examined. Based on these analyzed values, integrated values of NMR spectrum of CP/MAS on solid $^{29}Si$, the number of carbon atoms in $R^4$ of silanol group forming silicide $R^4SiY_3$, and the numbers of carbon atoms in $R^5$ and $R^6$ of silanol group forming silicide $R^5R^6SiZ_2$, the ratios of siloxane units $SiO_2$, siloxane units $R^1SiO_{1.5}$ and siloxane units $R^2R^3SiO$ were calculated.

TEST EXAMPLES 2-7

Syntheses of Organosilicone Fine Particles (P-2)-(P-7)

Organosilicone fine particles (P-2)-(P-7) were synthesized as done in Test Example 1 and observations, measurements and analyses similar to those done in Test Example 1 were carried out.

COMPARISON EXAMPLE 1

Synthesis of Fine Particles (R-1)

Ion exchange water 2000 g was placed in a reactor vessel and acetic acid 0.12 g and 10% aqueous solution of dodecylbenzene sodium sulfonate 7.1 g were added so as to make into a uniform aqueous solution. Tetraethoxy silane 270.0 g (1.30 mols), methyltrimethoxy silane 277.7 g (2.04 mols) and dimethyldimethoxy silane 44.4 g (0.37 mols) were added to this aqueous solution to carry out hydrolysis at 30° C. for 30 minutes. Ion exchange water 700 g and 30% aqueous solution of sodium hydroxide 1.86 g were placed in another reactor vessel to prepare a uniform aqueous solution. While this aqueous solution was being stirred, the aforementioned hydrolyzed liquid was gradually added to carry out a reaction at 15° C. for 5 hours and further for 5 hours at 80° C. to obtain a white suspension. After this white suspension was left quietly overnight, its liquid phase was removed by decantation, the white solid phase thus obtained was washed with water by a usual method and dried to obtain organosilicone fine particles (R-1). Observations, measurements and analyses similar to those in Test Example 1 were carried out on fine particles (R-1). Details of non-spherical hollow fine particles, etc. of the examples synthesized as above are shown together in Tables 1-3.

TABLE 1

| | Type of particles | Silanol group forming silicide $SiX_4$ | Silanol group forming silicide $R^4SiY_3$ | Silanol group forming silicide $R^5R^6SiZ_2$ | Catalyst for hydrolysis | Catalyst for condensation reaction | Surfactant |
|---|---|---|---|---|---|---|---|
| TE-1 | P-1 | SM-1/40 | SM-3/55 | SM-6/5 | CA-1/0.017 | CA-1/0.143 | A-1/0.124 |
| TE-2 | P-2 | SM-1/48 | SM-3/48 | SM-6/4 | CA-1/0.075 | CA-1/0.066 | A-1/0.035 |
| TE-3 | P-3 | SM-1/40 | SM-3/46 SM-4/6 | SM-6/8 | CA-2/0.022 | CA-2/0.210 | A-2/0.008 |
| TE-4 | P-4 | SM-2/35 | SM-3/53 SM-5/8 | SM-6/4 | CA-2/0.035 | CA-2/0.115 | A-2/0.016 |

TABLE 1-continued

|  | Type of particles | Silanol group forming silicide $SiX_4$ | Silanol group forming silicide $R^4SiY_3$ | Silanol group forming silicide $R^5R^6SiZ_2$ | Catalyst for hydrolysis | Catalyst for condensation reaction | Surfactant |
|---|---|---|---|---|---|---|---|
| TE-5 | P-5 | SM-2/44 | SM-3/37 SM-4/11 | SM-6/5 SM-7/3 | CA-1/0.008 | CA-2/0.015 | A-2/0.310 |
| TE-6 | P-6 | SM-2/45 | SM-3/40 SM-4/10 | SM-7/5 | CA-1/0.400 | CA-2/0.020 | A-1/0.025 |
| TE-7 | P-7 | SM-2/33 | SM-3/37 SM-5/26 | SM-7/4 | CA-2/0.030 | CA-1/0.011 | A-1/0.025 |
| CE-1 | R-1 | SM-1/35 | SM-3/55 | SM-6/10 | CA-3/0.020 | CA-1/0.094 | A-1/0.120 |

In Table 1:
TE: Test Example
CE: Comparison Example
Silicides are shown for "Type/Amount of use"
Catalysts and surfactants are shown for "Type/Concentration"
Amount of use: Molar % with respect to the total 100% of silanol group forming silicides used as material
Concentrations: Concentrations (mass %) with respect to silanol group forming silicides used as material
SM-1: Tetraethoxy silane
SM-2: Tetramethoxy silane
SM-3: Methyltrimethoxy silane
SM-4: Propyltributoxy silane
SM-5: Phenyltrimethoxy silane
SM-6: Dimethyldimethoxy silane
SM-7: Methylphenylmethoxyethoxy silane
CA-1: Sodium hydroxide
CA-2: Ammonium
CA-3: Acetic acid
A-1: Dodecylbenzene sodium sulfonate
A-2: Lauryl sodium sulfonate

TABLE 2

| Type of particles | | Siloxane units $SiO_2$ | | Siloxane units $R^1SiO_{1.5}$ | | Siloxane units $R^2R^3SiO$ | | Shape as a whole |
|---|---|---|---|---|---|---|---|---|
| | particles | Type | Ratio | Type | Ratio | Type | Ratio | |
| TE-1 | P-1 | S-1 | 40 | S-2 | 55 | S-5 | 5 | 1* |
| TE-2 | P-2 | S-1 | 48 | S-2 | 48 | S-5 | 4 | 1* |
| TE-3 | P-3 | S-1 | 40 | S-2 S-3 | 46 6 | S-5 | 8 | 1* |
| TE-4 | P-4 | S-1 | 35 | S-2 S-4 | 53 8 | S-5 | 4 | 1* |
| TE-5 | P-5 | S-1 | 44 | S-2 S-3 | 37 11 | S-5 S-6 | 5 3 | 1* |
| TE-6 | P-6 | S-1 | 45 | S-2 S-3 | 40 10 | S-6 | 5 | 1* |
| TE-7 | P-7 | S-1 | 33 | S-2 S-4 | 37 26 | S-6 | 4 | 1* |
| CE-1 | R-1 | S-1 | 35 | S-2 | 55 | S-5 | 10 | 2* |

In Table 2:
S-1: Anhydrous silicic acid unit
S-2: Methyl siloxane unit
S-3: Propyl siloxane unit
S-4: Phenyl siloxane unit
S-5: Dimethyl siloxane unit
S-6: Methylphenyl siloxane unit
Ratio: Molar %
1*: Tetrahedral shape as a whole, each surface being formed as a concave part 11 with an approximately circular opening
2* Shape of a rugby ball as a whole with a crack on surface in the longitudinal direction

TABLE 3

| | Type of particles | Average value of L in μm | Average of ratios m/L | Oil absorption (ml/100 g) |
|---|---|---|---|---|
| TE-1 | P-1 | 4.9 | 0.65 | 136 |
| TE-2 | P-2 | 2.8 | 0.76 | 144 |
| TE-3 | P-3 | 8.7 | 0.59 | 113 |
| TE-4 | P-4 | 18.6 | 0.53 | 96 |
| TE-5 | P-5 | 0.5 | 0.54 | 83 |
| TE-6 | P-6 | 0.9 | 0.48 | 71 |
| TE-7 | P-7 | 17.2 | 0.36 | 56 |
| CE-1 | R-1 | 2.5 | — | 42 |

In Table 3:
L: Maximum external diameter of individual particle (μm)
m: Maximum diameter of concave part 11 of individual particle (μm)

Part 2 (Preparation and Evaluation of Foundations)

Foundations were prepared by using organosilicone fine particles of each example as shown in Table 5 and evaluated as follows.

Preparation of Foundations

Pigments shows by numbers 1-7 in Table 4 were mixed together by using a mixer at the distribution ratio shown also in Table 4. Constituents numbered 8-12 at the mass ratios shown in Table 4 were separately taken, and after they were heated to 40° C. and mixed together, this was added to the aforementioned mixture prepared by the mixer to further mix them together. After the mixture thus obtained was left to be cooled, it was crushed and molded to prepare foundations.

TABLE 4

| Number | Composition | Mass ratio |
|---|---|---|
| 1 | Organosilicone fine particles to be evaluated | 7 |
| 2 | Titanium oxide | 10 |
| 3 | Talc | 20 |
| 4 | Sericite | 35 |
| 5 | Red iron oxide | 0.45 |
| 6 | Yellow iron oxide | 1 |
| 7 | Black iron oxide | 0.05 |
| 8 | Fluidic paraffin | 10 |
| 9 | Octylmethyl cyclotetra siloxane | 5 |
| 10 | Polyoxyalkylene modified silicone | 1.5 |

TABLE 4-continued

| Number | Composition | Mass ratio |
|---|---|---|
| 11 | Sorbitan aliphatic ester | 5 |
| 12 | Myristyl alcohol | 5 |

Evaluation of Foundations

The foundations described above were evaluated individually by twenty female panelists regarding their usability (extensions and expansions at the time of use) and feeling (stickiness, roughness and durability) according to the evaluation standards shown below. The results which have been rounded off are shown in Table 5 according to the following standards:

4: Very good

3: Good

2: Somewhat poor

1: Poor.

TABLE 5

| Type of organosilicone fine particles | Evaluation | | | |
|---|---|---|---|---|
| | Extensions and expansions | Stickiness | Roughness | Durability |
| TE-8 | P-1 | 4 | 4 | 4 | 4 |
| TE-9 | P-2 | 4 | 4 | 4 | 4 |
| TE-10 | P-3 | 3 | 4 | 4 | 3 |
| TE-11 | P-4 | 4 | 3 | 4 | 3 |
| TE-12 | P-5 | 4 | 3 | 3 | 3 |
| TE-13 | P-6 | 3 | 4 | 3 | 3 |
| TE-14 | P-7 | 3 | 3 | 3 | 3 |
| CE-2 | R-1 | 3 | 2 | 3 | 2 |
| CE-3 | R-2 | 2 | 1 | 1 | 3 |
| CE-4 | R-3 | 1 | 1 | 1 | 2 |
| CE-5 | R-4 | 1 | 1 | 1 | 1 |

In Table 5:
R-2: Spherical silicone fine particles (Tospearl 120 (tradename) produced by Momentive Performance Materials Inc.)
R-3: Spherical vinyl fine particles (Ganz Pearl GSM1261 (tradename) produced by Ganz Chemical Co., Ltd.)
R-4: Talc Table 5 clearly shows that organosilicone fine particles according to this invention exhibit superior results in usability and feeling when used as cosmetic materials.

Part 3 (Preparation and Evaluation of Polycarbonate Resin Compositions)

Polycarbonate resin compositions were prepared by using each example of organosilicone fine particles shown in Table 6 and evaluated.

Preparation of Polycarbonate Resin Compositions

Organosilicone fine particles (0.7 parts) shown in Table 7 were added to polycarbonate resin (Panlite K1285 (tradename) produced by Teijin Chemicals, Ltd.) (100 parts) and after they were mixed together, they were melted and kneaded together at resin temperature of 280° C. by using a biaxial extruder (40 mmΦ) equipped with vent to obtain pellets of polycarbonate resin composition by extrusion. These pellets were molded by using an injection molding machine at cylinder temperature of 230° C. and mold temperature of 60° C. and test plates with thickness of 3 mm and width 200 mm were produced.

Evaluation of Polycarbonate Resin Compositions

The aforementioned test pieces produced by using pellets as polycarbonate resin compositions were used to measure their total light transmittance and haze and also to obtain their heat-resistant colorability. The results are shown in Table 6.

Total Light Transmittance and Haze

Total light transmittance and haze were measured according to JIS-K7105 (1981) by using NDH-2000 (tradename) produced by Nippon Denshoku Industries Co., Ltd.

Heat-resistant Colorability

Each test piece was placed inside a heated air circulating oven at temperature of 80° C. and maintained there for 180 minutes. The degree of coloration by heating was measured in terms of the b-value by using a color meter (CR-300 (tradename) produced by Minolta Co., Ltd.). The value of $\Delta b$ was calculated according to JIS-Z8729 (2004) from the formula $\Delta b = b^2 - b^1$ where $b^1$ is the b-value of the sample film before the heat treatment and $b^2$ is the b-value of the sample film after the heat treatment.

TABLE 6

| | Type of organosilicone fine particles | Total light transmittance (%) | Haze | Heat-resistant colorability ($\Delta b$) |
|---|---|---|---|---|
| TE-15 | P-1 | 93.1 | 90.1 | 0.0 |
| TE-16 | P-2 | 92.8 | 90.3 | 0.0 |
| TE-17 | P-3 | 88.8 | 86.5 | 0.1 |
| TE-18 | P-4 | 87.1 | 85.8 | 0.2 |
| TE-19 | P-5 | 85.4 | 83.4 | 0.2 |
| TE-20 | P-6 | 85.8 | 84.1 | 0.3 |
| TE-21 | P-7 | 85.7 | 82.9 | 0.4 |
| CE-6 | R-1 | 81.8 | 80.2 | 0.2 |
| CE-7 | R-2 | 82.2 | 78.9 | 0.2 |
| CE-8 | R-3 | 81.7 | 78.7 | 4.3 |
| CE-9 | R-5 | 78.1 | 76.9 | 2.2 |

In Table 6:
R-5: Calcium carbonate
Total light transmittance: %
Heat-resistant colorability: Value of $\Delta b$ The results shown in Table 6 clearly indicate that organosilicone fine particles of this invention can fully respond to the advanced requirements of recent years when used for resin compositions.

Part 4 (Preparation and Evaluation of Paint Compositions)

Paint compositions were prepared by using each example of organosilicone fine particles shown in Table 7 and evaluated.

Preparation of Paint Compositions

Organosilicone fine particles (7 parts) according to each example shown in Table 7 were added to acryl resin solution with effective component 70% (ACRYDIC A-416-70S (tradename) produced by DIC Corporation) (100 parts) and were mixed together with stirring for 10 minutes by using a homomixer at 2000 rpm to obtain a paint composition.

Evaluation of Paint Compositions

Storage stability of the paint compositions thus prepared was evaluated as follows and the evaluation results are shown in Table 7.

Evaluation of Paint Film

An aluminum panel was coated with each of the prepared paint compositions and hardened by heating for 30 minutes inside an isothermal tank with the temperature set at 150° C. Dispersibility, matte effect and factual sense of each hardened paint film were evaluated according to the following standards. The results are shown in Table 7.

Evaluation of Storage Stability

Paint compositions were maintained quietly at a room temperature and the dispersed condition of the organosilicone fine particles in the paint compositions after 5 hours was evaluated according to the following standards by visually observing.

A: Very good (organosilicone fine particles uniformly dispersed after 5 hours)

B: Good (no deposition of organosilicone fine particles observed after 2 hours but some depositions were observable after 5 hours)

C: Poor (precipitation of organosilicone fine particles observed after 2 hours)

Evaluation of Dispersibility

Dispersed conditions of organosilicone fine particles in the hardened paint films were observed by using an optical microscope and evaluated according to the following standards.

A: Good (no aggregation of organosilicone fine particles observed, particles being uniformly dispersed)

B: Poor (organosilicone fine particles aggregated)

Evaluation of Matte Effect

Luster conditions of the hardened paint films were visually observed and evaluated according to the following standards.

A: Very good (surface being uniform without luster)
B: Fair (surface having some luster marks)
C: Poor (surface being uniform with luster)

Evaluation of Factual Sense

The hardened paint films were touched by hand and the feeling was evaluated according to the following standards.

A: Good (smooth feeling)
B: Poor (rough feeling)

TABLE 7

|  | Type of organosilicone fine particles | Evaluation | | | |
| --- | --- | --- | --- | --- | --- |
|  |  | Storage stability | Dispersibility | Matte effect | Factual sense |
| TE-22 | P-1 | A | A | A | A |
| TE-23 | P-2 | A | A | A | A |
| TE-24 | P-3 | B | A | A | A |
| TE-25 | P-4 | B | A | A | A |
| TE-26 | P-5 | B | A | B | A |
| TE-27 | P-6 | B | A | B | A |
| TE-28 | P-7 | B | A | B | A |
| CE-10 | R-1 | B | B | C | A |
| CE-11 | R-2 | B | B | C | A |
| CE-12 | R-3 | B | A | C | B |
| CE-13 | R-6 | B | B | C | A |

In Table 7:
R-6: Spherical complex silicone particles (KMP-605 (tradename) produced by Shin-Etsu Chemical Co., Ltd.)

What is claimed is:

1. Organosilicone fine particles with tetrahedral general shapes having surfaces each comprising a concave part with an approximately circular opening,
   wherein the maximum external diameters L of the organosilicone fine particles have an average value in the range of 0.5-20 μm, the average value of the maximum external diameters L being taken from arbitrarily selected 20 of a scanning electron microscope photograph image of said organosilicone fine particles;
   wherein the ratio m/L of the maximum diameter m of the concave part with respect to the maximum external diameter L has an average value in the range of 0.3-0.8 taken from arbitrarily selected 20 of a scanning electron microscope photograph image of said organosilicone fine particles;
   wherein oil absorption of said organosilicone fine particles is 50-150 ml/100 g; and
   wherein said organosilicone fine particles comprise siloxane units forming a polysiloxane cross-link structure including siloxane units $SiO_2$ in an amount of 30-50 molar %, siloxane units $R^1SiO_{1.5}$ in an amount of 45-65 molar % and siloxane units $R^2R^3SiO$ in an amount of 3-9 molar % so as to be a total of 100 molar %, wherein $R^1$, $R^2$ and $R^3$ are each alkyl group with 1-4 carbon atoms or phenyl group.

2. A method of producing the organosilicone fine particles of claim 1, said method comprising the steps of:
   using silanol group forming silicide $SiX_4$ in an amount of 30-50 molar %, silanol group forming silicide $R^4SiY_3$ in an amount of 45-65 molar % and silanol group forming silicide $R^5R^6SiZ_2$ in an amount of 3-9 molar % so as to be a total of 100 molar %;
   generating a silanol compound by causing silanol group forming silicide $SiX_4$ and silanol group forming silicide $R^5R^6SiZ_2$ to contact water in the presence of a basic catalyst so as to undergo hydrolysis; and
   causing a condensation reaction of said silanol compound with silanol group forming silicide $R^4SiY_3$ in an aqueous condition in the presence of a basic catalyst and an anionic surfactant;
   wherein $R^4$, $R^5$ and $R^6$ are each alkyl group with 1-4 carbon atoms or phenyl group, and X, Y and Z are each alkoxy group with 1-4 carbon atoms, alkoxyethoxy group having alkoxy group with 1-4 carbon atoms, acyloxy group with 2-4 carbon atoms, N,N- dialkylamino group having alkyl group with 1-4 carbon atoms, hydroxyl group, halogen atom or hydrogen atom.

3. A cosmetic material containing the organosilicone fine particles of claim 1 in an amount of 0.1-10 mass %.

4. A resin composition containing the organosilicone fine particles of claim 1 in an amount of 0.1-10 mass %.

5. A paint composition containing the organosilicone fine particles of claim 1 in an amount of 0.1-15 mass %.

* * * * *